(12) United States Patent
Sherman et al.

(10) Patent No.: US 8,535,330 B2
(45) Date of Patent: Sep. 17, 2013

(54) ARTHROSCOPIC TIBIAL SIZER

(75) Inventors: Gary Scott Sherman, Naples, FL (US); Ricardo Albertorio, Naples, FL (US)

(73) Assignee: Arthrex, Inc., Naples, FL (US)

( * ) Notice: Subject to any disclaimer, the term of this patent is extended or adjusted under 35 U.S.C. 154(b) by 603 days.

(21) Appl. No.: 12/819,030

(22) Filed: Jun. 18, 2010

(65) Prior Publication Data

US 2011/0004260 A1 Jan. 6, 2011

Related U.S. Application Data

(60) Provisional application No. 61/222,755, filed on Jul. 2, 2009.

(51) Int. Cl.
*A61B 17/56* (2006.01)
*A61B 5/107* (2006.01)

(52) U.S. Cl.
USPC .......................... 606/102; 606/86 R; 600/587

(58) Field of Classification Search
USPC ............. D24/140; 33/501.45, 512, 542, 545, 33/555.1, 555.4; 600/587; 606/86 R, 102, 606/87–88; 623/20.14–20.16, 20.21, 20.3, 623/20.31–20.32, 20.35
See application file for complete search history.

(56) References Cited

U.S. PATENT DOCUMENTS

| | | | |
|---|---|---|---|
| 5,366,460 A | 11/1994 | Eberbach | |
| 7,172,599 B2* | 2/2007 | Steffensmeier et al. | 606/102 |
| 7,857,851 B2* | 12/2010 | Zannis et al. | 623/14.12 |
| 2004/0133229 A1 | 7/2004 | Lambrecht et al. | |
| 2007/0161930 A1* | 7/2007 | Reitzig et al. | 600/594 |
| 2007/0233128 A1 | 10/2007 | Schmieding et al. | |
| 2008/0147076 A1 | 6/2008 | Geisert et al. | |
| 2008/0275512 A1* | 11/2008 | Albertorio et al. | 606/86 R |

* cited by examiner

*Primary Examiner* — Nicholas Woodall
*Assistant Examiner* — Larry E Waggle, Jr.
(74) *Attorney, Agent, or Firm* — Dickstein Shapiro LLP

(57) ABSTRACT

An arthroscopic tibial sizer provided with a collapsible loop (for example, a nitinol loop) and a pin indicator located at about the center of the collapsible loop. The collapsible loop is formed of a flexible wire (for example, nitinol wire) and is designed to collapse so that it can be inserted through an arthroscopic portal and into the joint, and then to expand out to its original diameter once inside the joint space, for visual sizing. The collapsible loop may be provided in various diameters (i.e., 14, 17 or 20 mm, for example) to match various implant sizes. The pin indicator indicates the center of the loop and provides identification of the center of the tibial defect.

6 Claims, 4 Drawing Sheets

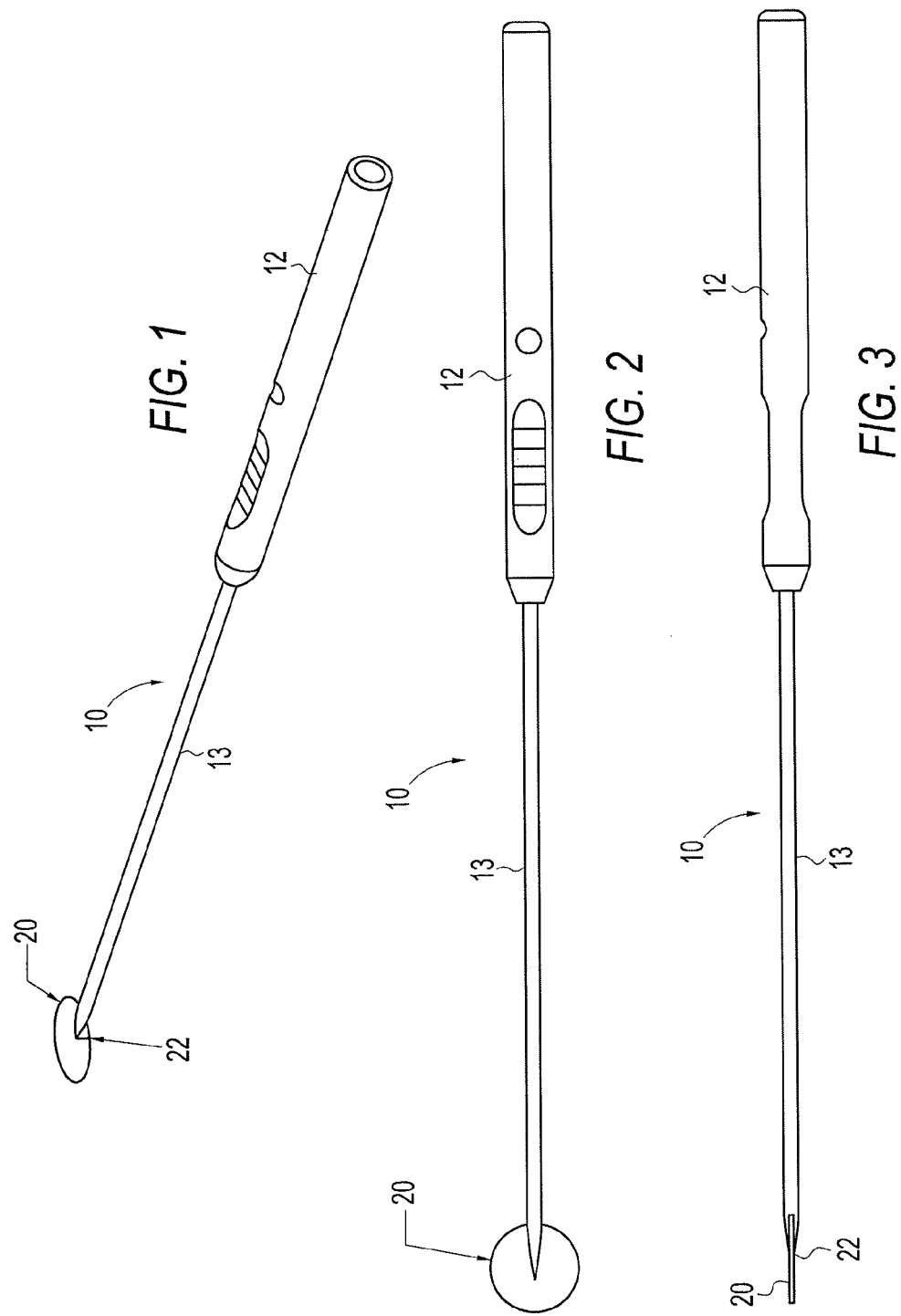

FIG. 4
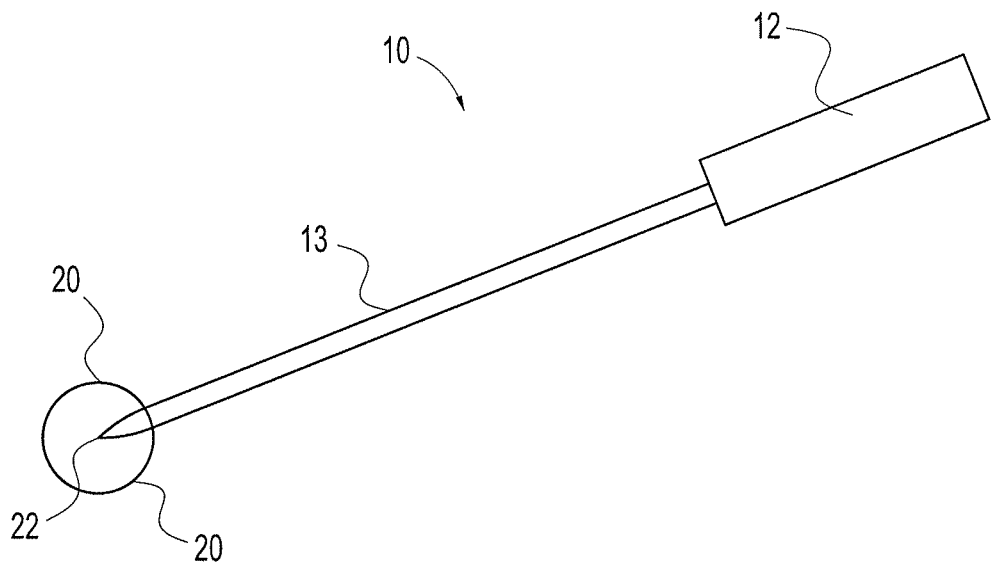
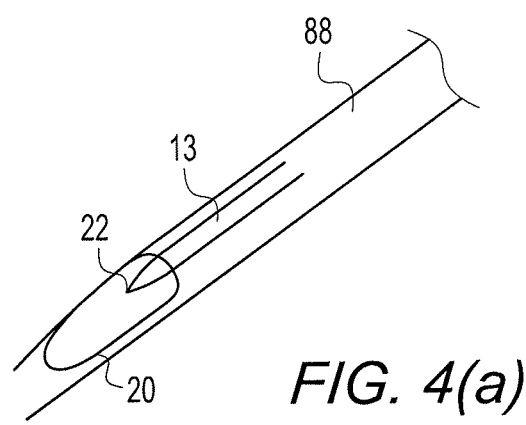
FIG. 4(a)

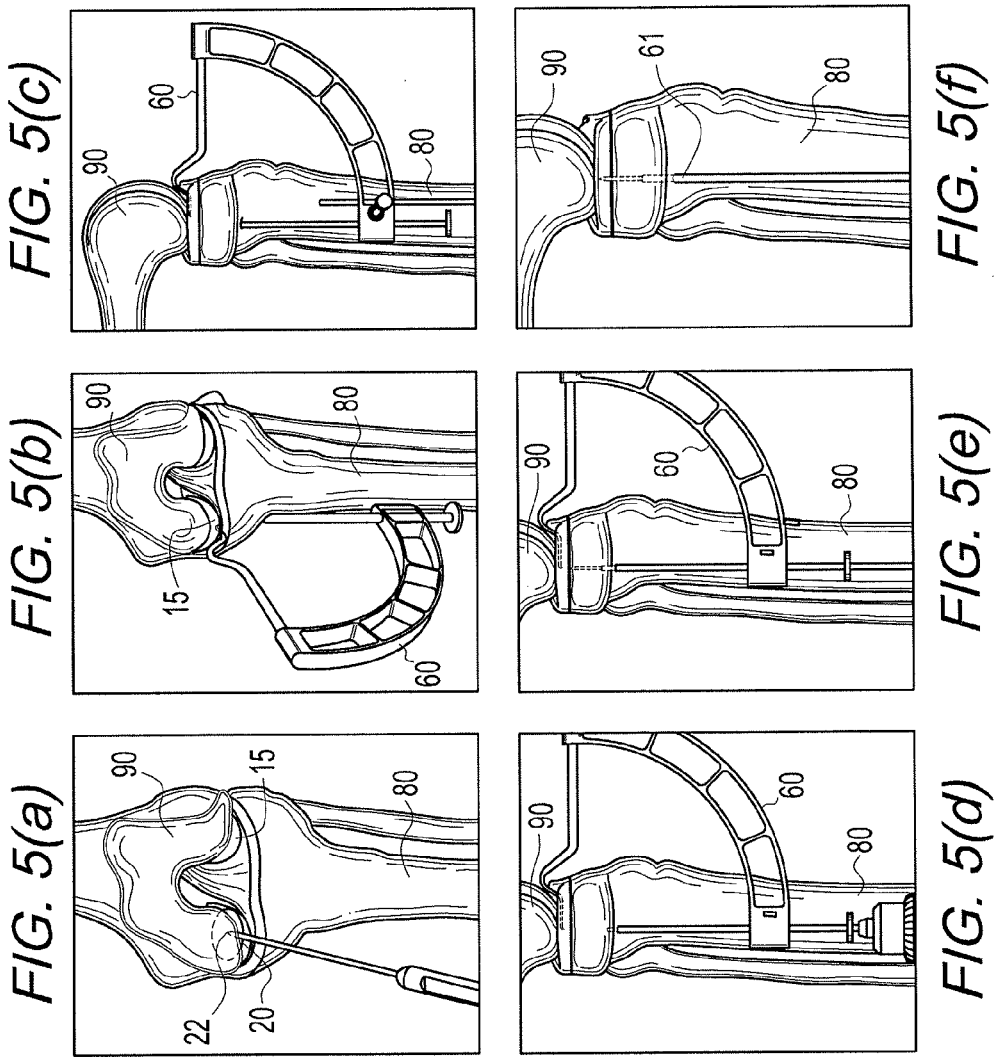

ARTHROSCOPIC TIBIAL SIZER

CROSS-REFERENCE TO RELATED APPLICATIONS

This application claims the benefit of U.S. Provisional Application Ser. No. 61/222,755, filed Jul. 2, 2009, the entire disclosure of which is incorporated by reference herein.

FIELD OF THE INVENTION

The present invention relates to the field of arthroscopic surgery and, more particularly, to improved instrumentation for reconstructive knee surgery.

BACKGROUND OF THE INVENTION

Partial knee replacement surgery (also called unicompartmental knee arthroplasty) is known in the art for the treatment of osteoarthritis of the knee joint. During partial knee replacement surgery, the bone and cartilage on the end of the femur and top of the tibia are removed. A knee replacement implant made of various biocompatible materials such as metal or plastic is then placed to function as a new knee joint. Depending on the condition of the cartilage on the undersurface of the kneecap, the cartilage may also be replaced. The knee replacement implant typically comprises (i) a femoral component which fits on the femur, (ii) a tibial component which fits on the tibia, and optionally (iii) a patellar component, made of plastic and which replaces the cartilage on the undersurface of the kneecap, and optionally (iv) a plastic insert which fits between the femoral and tibial components.

Placement of the knee replacement implant typically involves the steps of: (i) forming a tibial socket; (ii) performing at least one cut on the femoral condyle; and (iii) placing implants or components into the socket on the tibial plateau and into the femoral cut. These steps are performed using precise instruments to create exact surfaces to accommodate the implant. For example, instrumentation and apparatus for arthroscopic unicompartmental knee surgery (which include a femoral component and a tibial component) are described in U.S. Patent Application Publication No. 2008/0275512, the disclosure of which is incorporated by reference in its entirety herewith.

SUMMARY OF THE INVENTION

The present invention provides techniques and apparatus for unicompartmental knee surgery by utilizing a novel arthroscopic tibial sizer that allows the surgeon and/or medical personnel to visually determine the correct size implant for the tibial plateau.

The arthroscopic tibial sizer of the present invention is provided with a collapsible loop (for example, a nitinol loop) and a pin indicator located at about the center of the collapsible loop. The collapsible loop is formed of a flexible wire (for example, nitinol wire) and is designed to collapse so that it can be inserted through an arthroscopic portal and into the joint, and then to expand out to its original diameter once inside the joint space, for visual sizing. The collapsible loop may be provided in various diameters (i.e., 14, 17 or 20 mm, for example) to match various implant sizes. The pin indicator indicates the center of the loop and provides identification of the center of the tibial defect.

By utilizing the arthroscopic tibial sizer of the present invention in lieu of a typical sizing instrument used in the art (for example, a tibial sizing spoon), the surgeon can visualize the correct size implant for the unicompartmental knee surgery based on the wire (collapsible loop) in relation to the tibial plateau, and can also assess the center of the defect based on the location of the pin indicator.

The present invention also provides a method of arthroscopically preparing both the femur and tibia to accept a unicompartmental implant that covers the contact area between femur and tibia. The method includes the step of determining the size of the tibial implant or component by employing a tibial sizer comprising a collapsible loop (for example, a nitinol loop) and a pin indicator located at about the center of the collapsible loop, the collapsible loop being designed to collapse so that it can be inserted through an arthroscopic portal and into the joint, and then to expand out to its original diameter once inside the joint space.

Other features and advantages of the present invention will become apparent from the following description of the invention which refers to the accompanying drawings.

BRIEF DESCRIPTION OF THE DRAWINGS

FIG. 1 illustrates a perspective view of an arthroscopic tibial sizer of the present invention;

FIG. 2 illustrates a top view of the arthroscopic tibial sizer of FIG. 1;

FIG. 3 illustrates a side view of the arthroscopic tibial sizer of FIG. 1;

FIG. 4 illustrates another schematic view of the collapsible loop of the arthroscopic tibial sizer of FIG. 1 (in the relaxed or expanded or original configuration);

FIG. 4(a) illustrates a view of a most distal end of the shaft of the tibial sizer of FIG. 4, with the collapsible loop in the collapsed configuration (i.e., during insertion and passage through a portal, cannula or socket); and FIGS. 5(a)-(f) illustrate subsequent views of a knee undergoing tibial sizing with the arthroscopic tibial sizer of FIG. 1, during knee replacement surgery according to an embodiment of the present invention, and illustrating the tibial sizer introduced into the joint space through an arthroscopic portal.

DETAILED DESCRIPTION OF THE INVENTION

Figure 6:
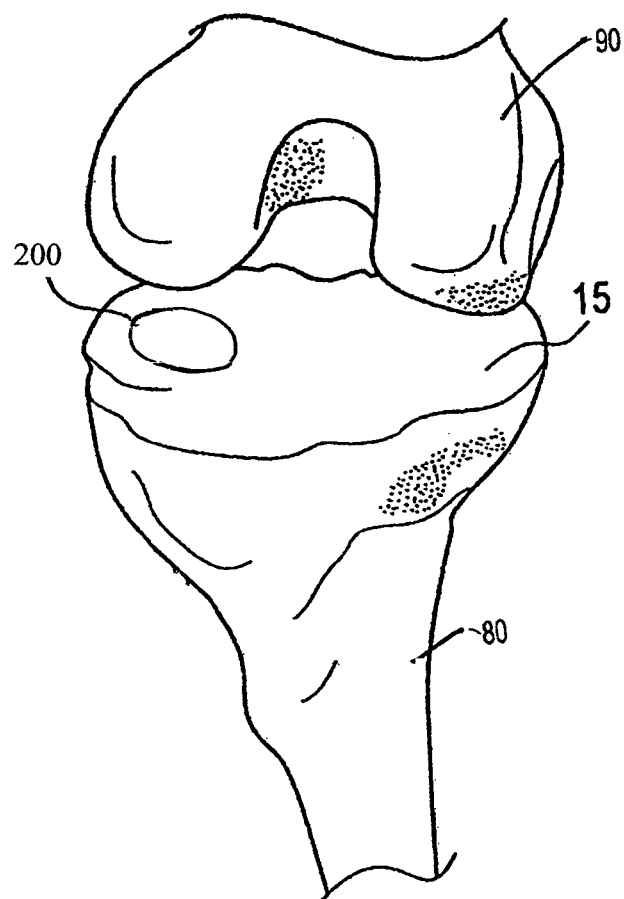
FIG. 6 illustrates a schematic view of a knee with a tibial component 200 sized with the tibial sizer of FIG. 1 and by the method of FIGS. 5(a)-5(f).

Referring now to the drawings, where like elements are designated by like reference numerals, FIGS. 1-4(a) illustrate various views of arthroscopic tibial sizer 10 of the present invention (with the arthroscopic tibial sizer 10, with the collapsible loop illustrated in the collapsed and relaxed configuration). FIGS. 5(a)-5(f) illustrate subsequent views of a knee undergoing tibial sizing with the arthroscopic tibial sizer 10 of FIG. 1, illustrating the tibial sizer 10 introduced into the joint space through an arthroscopic portal (to determine the location of the tibial tunnel or socket to be made) during an exemplary knee replacement surgery.

As shown in FIGS. 1-4(a), the arthroscopic tibial sizer 10 of the present invention is provided with handle 12 and shaft 13, and a collapsible loop 20 (for example, a nitinol loop 20) attached to the shaft 13. A pin indicator 22 is located at a most distal end of the shaft 13 and at about the center of the collapsible loop 20. The collapsible loop 20 is preferably formed of a flexible wire (for example, nitinol wire) and is designed to collapse so that it can be inserted through an arthroscopic portal and into the joint, and then to expand out to its original diameter once inside the joint space, for visual sizing. The collapsible loop 20 may be provided in various diameters (i.e., 14, 17 or 20 mm, for example) to match various implant sizes. As shown in FIGS. 1-4(a), the collapsible loop 20 is an uninterrupted loop. The pin indicator 22 indicates the center of the loop and provides identification of the center of the tibial defect on tibial plateau 15 (i.e., identifies the dimensions of the tibial defect to further determine the location and dimensions of the tibial tunnel or socket, and of the tibial implant).

Arthroscopic tibial sizer 10 shown in FIGS. 1-4(a) allows the surgeon or medical personnel to visually determine the correct size implant for the tibial plateau 15. By utilizing the arthroscopic tibial sizer 10 of the present invention in lieu of a typical sizing instrument used in the art (for example, a tibial sizing spoon), the surgeon can visualize the correct size implant for the unicompartmental knee surgery based on the wire 20 (collapsible loop 20) in relation to the tibial plateau 15, and can also assess the center of the defect (and the dimensions of the tunnel or socket to be formed) based on the location of the pin indicator 22. FIG. 4(a) illustrates the loop 20 of the sizer 10 in the collapsed configuration, i.e., inserted through an arthroscopic portal 88 (or cannula) and into a joint (such as the knee joint). FIG. 4 illustrates the loop 20 of the sizer 10 in the expanded, relaxed configuration (i.e., springing open once inside the joint space and out of the arthroscopic portal).

Once the size of the defect has been assessed, the formation of the tibial socket or tunnel and of the femoral cut is conducted as known in the art. The formation of the tibial tunnel or socket may be conducted before or after the formation of the femoral cut and by various methods known in the art (such as retrograde cutting, for example). The femoral condyle is cut to accept an appropriate sized component. Exemplary steps of an arthroscopic unicompartmental knee surgery (which include a femoral component and a tibial component) are described in U.S. Patent Application Publication No. 2008/0275512, the disclosure of which is incorporated by reference in its entirety herewith.

After completing the cuts, femoral and tibial implants or components can be pulled into place with FiberWire through transosseous holes. Cement may be injected through the holes to prepare a mantel over which the implant is placed. External guides may be used for targeting pin placement and to guide milling of sockets (angles). Femoral implants may be cemented, press fit, and/or made up of one or more interlocking pieces. Material may be cobalt chrome alloy or similar compositions. Tibial components may be press fit or cemented and/or made of polymer (machined or compression molded). Tibial components may also be metal backed. For added fixation, the femoral and/or tibial components may be secured with buttons or screws.

FIGS. 5(a)-(f) illustrate exemplary, subsequent views of a knee undergoing tibial sizing with the arthroscopic tibial sizer 10 of FIG. 1 (during knee replacement surgery according to an embodiment of the present invention), and illustrating the tibial sizer 10 introduced into the joint space through an arthroscopic portal to determine where the socket/tunnel should be made.

FIGS. 5(a)-(f) illustrate femur 90 and tibia 80 with tibial plateau 15 having a defect undergoing tibial sizing with the instrument 10 of the present invention (to determine where the tibial socket/tunnel should be made). FIG. 5(a) illustrates the loop 20 of the sizer 10 in the expanded, relaxed configuration (i.e., springing open once inside the joint space and after passing through an arthroscopic portal). The center of the defect (and the location of the tibial tunnel) is assessed based on the location of the pin indicator 22.

The steps and instrumentation for arthroscopic unicompartmental knee surgery (which include a femoral component and a tibial component) illustrated in FIGS. 5(b)-(f) are similar to those described in U.S. Patent Application Publication No. 2008/0275512, the disclosure of which is incorporated by reference. As shown in FIGS. 5(b)-(f) and as described in U.S. Patent Application Publication No. 2008/0275512, the tibial socket may be formed in a retrograde manner, by employing a retrograde drill cutter which is inserted into the joint and threaded onto the pin tip arthroscopically in a manner similar to the insertion of the retrograde drill cutter in the technique for ACL RetroConstruction by Arthrex, Inc., Naples, Fla., as disclosed in U.S. Patent Application Publication No. 2007/0233128, the disclosure of which is incorporated in its entirety by reference herein. As described and claimed in U.S. Patent Application Publication No. 2007/0233128, the retrograde insertion technique involves threading an appropriate diameter drill cutter onto an insertion post connected to a C-Ring 60 (FIG. 5(b)), inserting the mounted drill cutter into the knee joint through the anteromedial portal, and advancing the drill pin through a guide sleeve connected to the C-Ring 60, through the tibia and into the joint to engage the drill cutter. FIG. 5(f) illustrates an exemplary drill 61 provided over a guide pin to form the tibial socket.

The tibial socket may be alternatively formed by employing a flip retrograde cutter having a flip cutting blade that is configured to articulate between at least a first "straight" position aligned with the longitudinal axis of the cutting instrument and a second "flip" position, for example, perpendicular to the longitudinal axis of the cutting instrument. The tibial socket is formed by advancing the flip retrograde cutter through the tibial and into the knee joint, flipping the blade into the second "flip" position, and then rotating the instrument while pulling back, to cut a tibial socket in a retrograde manner. All subsequent steps for knee reconstruction may proceed as detailed in U.S. Patent Application Publication No. 2008/0275512.

Subsequent to the formation of the tibial socket, and as detailed in U.S. Patent Application Publication No. 2008/0275512 (the disclosure of which is incorporated by reference), the depth of the tibial socket may be measured using a depth gage and a tibial trial may be used to gage the tibial socket. A femoral assembly including a template, a plurality of drill pins and a plurality of corresponding cutters may be employed to create a femoral trough on a curvature of a femoral condyle. The femoral trough may be formed either before or after the formation of the tibial socket.

As also detailed in U.S. Patent Application Publication No. 2008/0275512, the cutters are placed with depth stop over pins and bored until the depth stop contacts the femur. In this manner, the depth of both holes is controlled and proper seating of the femoral component is insured. The hole formed by one of the cutters is deeper than the hole made by the other one of the cutters. After reaming the two holes in the femoral condyle, the cutters are removed and an osteotomy plier with a cannulation is advanced over the drill pin remaining in the femoral condyle. The bone between the hole created by cutters (which form an hourglass shaped cavity) is removed by closing the jaws of the osteotomy plier using the handles of the instrument, to create an oval shaped trough. The femoral component may be subsequently inserted by tapping it into place with a femoral impactor to obtain a reconstructed femur 90. The tibial component may be either screwed into the socket or pulled into the tibial socket in a retrograde manner with suture. Cement may be injected through the holes to prepare a mantel over which the components are placed. External guides may be used for targeting pin placement and to guide milling of sockets (angles). The femoral component may be cemented, press fit, and/or made be formed of one or more interlocking pieces. The tibial component is screwed into the tibial socket, press fitted or cemented. For added fixation, the femoral and/or tibial components may be secured with buttons or screws. FIG. 6 illustrates an exemplary tibial component 200 secured into the tibial plateau 15 of tibia 80 by the methods of the present invention.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of knee reconstruction, the method comprising the steps of:

inserting a tibial sizer through an arthroscopic portal into a knee joint, the tibial sizer comprising a flexible, uninterrupted loop attached to a handle, and a point indicator indicating a center of the loop, the loop being configured to collapse while being inserted through the arthroscopic portal and to expand to its original diameter while exiting the arthroscopic portal and once within the knee joint;

assessing dimensions of a defect in the tibial plateau by matching the point indicator with a center of the defect in the tibial plateau;

forming a tibial socket in the tibia based on the dimensions of the defect;

forming at least one cut on the femoral condyle; and securing at least at a tibial component of a knee implant in the socket of the tibia, wherein the size of the tibial component is based upon the dimensions of the defect in the tibial plateau.

2. The method of claim 1, wherein the tibial socket is formed by retrograde drilling.

3. The method of claim 1, wherein the flexible loop is a circular wire loop.

4. The method of claim 1, wherein the flexible loop is a nitinol loop.

5. The method of claim 1, wherein the flexible loop has a diameter of about 14 mm, about 17 mm or about 20 mm.

6. The method of claim 1, further comprising the step of providing identification of the center of the defect in the tibial plateau by the point indicator.

* * * * *